United States Patent [19]

Shearing

[11] Patent Number: 4,704,124
[45] Date of Patent: Nov. 3, 1987

[54] INTRAOCULAR LENS

[76] Inventor: Steven P. Shearing, 2575 Lindell, Las Vegas, Nev. 89102

[21] Appl. No.: 6,803
[22] Filed: Jan. 27, 1987

Related U.S. Application Data

[60] Division of Ser. No. 693,108, Jan. 22, 1985, Pat. No. 4,657,546, which is a continuation-in-part of Ser. No. 511,906, Jul. 8, 1983, abandoned.

[51] Int. Cl.$^4$ .............................................. A61F 2/16
[52] U.S. Cl. ......................................................... 623/6
[58] Field of Search .......................................... 623/6

[56] References Cited

U.S. PATENT DOCUMENTS

| | | | |
|---|---|---|---|
| 4,073,014 | 2/1978 | Poler | 623/6 |
| 4,092,743 | 6/1978 | Kelman | 623/6 |
| 4,159,546 | 7/1979 | Shearing | 623/6 |
| 4,316,291 | 2/1982 | Severin | 623/6 |
| 4,451,938 | 6/1984 | Kelman | 623/6 |

FOREIGN PATENT DOCUMENTS 0099641  2/1984  European Pat. Off. ............. 623/6

*Primary Examiner*—Ronald L. Frinks
*Attorney, Agent, or Firm*—Seiler, Quirk & Tratos

[57] ABSTRACT

An improved intraocular lens comprises a plurality of lens segments secured in a flexible and distortable frame member whereby the lens may be temporarily folded for insertion into the eye through a relatively small corneal incision. The preferred lens segments have a thickness of about 1.0 mm or less and comprise an optical material having an index of refraction of 1.5 or more.

3 Claims, 11 Drawing Figures

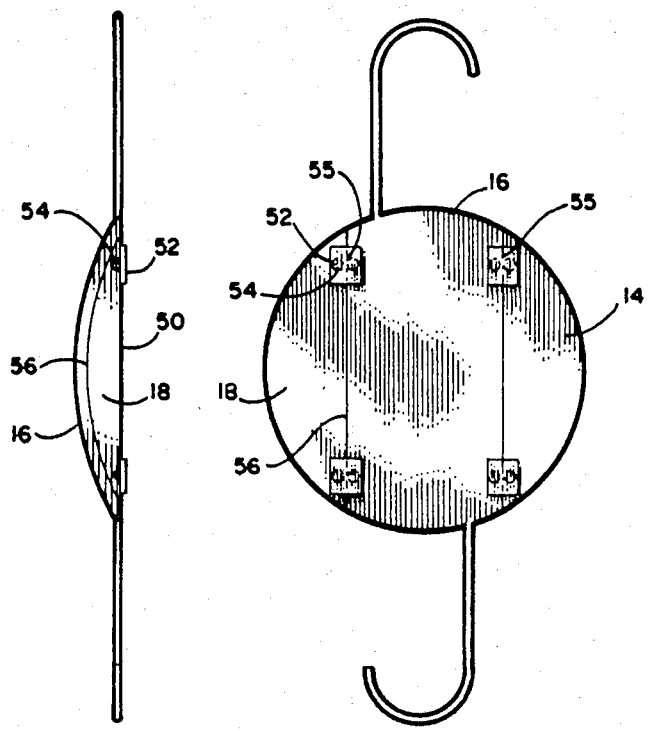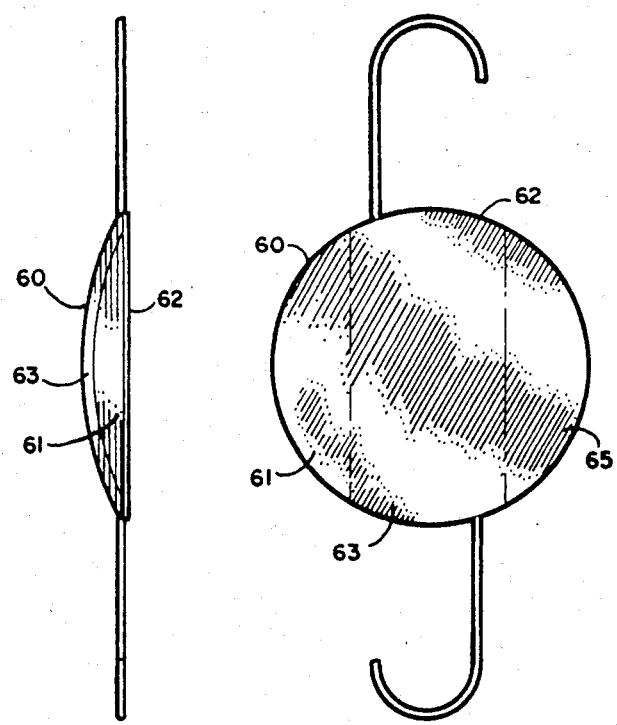

INTRAOCULAR LENS

This application is a divisional of co-pending application Ser. No. 06/693,108, filed Jan. 22, 1985, now U.S. Pat. No. 4,657,546 which in turn is a continuation-in-part of co-pending application Ser. No. 06/511,906, filed July 8, 1983, now abandoned.

BACKGROUND OF THE INVENTION

In my prior U.S. Pat. No. 4,159,546, there is disclosed an intraocular lens for being inserted into the posterior chamber of the eye. The use of intraocular lenses, for implantation in both the anterior or posterior chamber, has more recently become widely and successfully used following cataract surgery. In such surgery, it is most desirable to create a minimal corneal incision in order to reduce trauma to the cornea. Although recent developments in surgical apparatus have allowed for removal of the cataract through an incision as small as about 2.5 mm, where an intraocular lens is to be inserted, larger incisions are required. Although some intraocular lenses have been proposed having an optic lens body as small as about 4 mm, lens body diameters of between about 5 and about 7 mm are usually preferred. However, for insertion of such a lens, the incision must be large enough to allow insertion of the lens therethrough.

In an attempt to reduce the size of the corneal incision, in my aforesaid application there is disclosed a segmented lens, allowing for smaller individual lens segments to be inserted through a relatively small incision, after which the lens segments are to be assembled in the eye to form the lens body. A similar lens is shown in U.S. patent No. 4,451,938. Although the use of such a lens appears to be beneficial, in practice it is found to present substantial difficulties in attempting to assemble the segments in the eye, particularly the posterior chamber. It is a purpose of the invention to provide a lens which obviates the aforesaid assembly difficulties.

SUMMARY OF THE INVENTION

The intraocular lens of the present invention comprises a lens body having a plurality of lens segments held together by flexible, distortable and preferably memory-retaining members. The lens material is preferably of a relatively high index of refraction with the thickest part of the lens being about 1 mm or less, substantially less than lens used heretofore. The lens may be temporarily distorted by folding or bending the flexible frame or members to overlap the segments, and inserted into the eye through a relatively small corneal incision. Once placed within the eye, and the distorting pressure released, the lens segments will be readily returned to their original planar relationship to reform the lens body. In another embodiment, a single lens segment is supported in a modified flexible and foldable frame member, FIG. 13 being a sectional view taken along lines B—B of FIG. 12.

BRIEF DESCRIPTION OF THE DRAWINGS

FIGS. 8 and 9 illustrate still another embodiment of the invention incorporating flexible hinges for securing segmented lens;

FIGS. 10 and 11 illustrate another embodiment of the invention utilizing a thin sheet of flexible optical material secured to the lens body overlying and securing the lens segments.

DETAILED DESCRIPTION OF THE INVENTION

In its broad application, the improvement of the invention comprises an intraocular lens having a plurality of lens segments which are normally held together in a single plane to form a planar lens body and having means secured to the lens segments to assist in maintaining them in such a planar relationship when the lens is properly implanted in the eye. Such a means must be flexible and temporarily distortable to allow the lens segments to be folded in an overlapping relationship during insertion of the lens body through a corneal incision. The means for securing or holding the lens segments together is also preferably memory retaining whereby it will return to its original shape when distorting pressure is released.

In order to achieve a folded lens assembly within suitable dimensions, the greatest thickness of the center lens segment, the thickest segment in a convex lens, should be about 1 mm or less. The preferred lens is also formed of three lens segments, a center segment and two side segments, so that the center segment is free of distortion and without segment interfaces at or very near the center of the lens. To produce lens of maximum 1 mm or less thickness will require use of optical quality material of relatively high index of refraction of 1.5 or greater and more preferably 1.6 or more. Suitable materials having such a high refractive index include optical quality polysulfone and high quality optical glass. The width of the lens segments should also be such that the two side segments can be folded without being substantially overlapped which would unduly increase the cross-sectional thickness of the folded lens, thereby at least partially defeating the purpose of the invention. Thus, for example, where the overall lens body diameter is between about 4 and 7 mm, preferably about 6.0 mm, a center lens segment having a width between about 2.5 and 3.5 mm with side segments each being between about 1.25 and about 2.0 mm are quite suitable to avoid such overlap.

Figure 1:
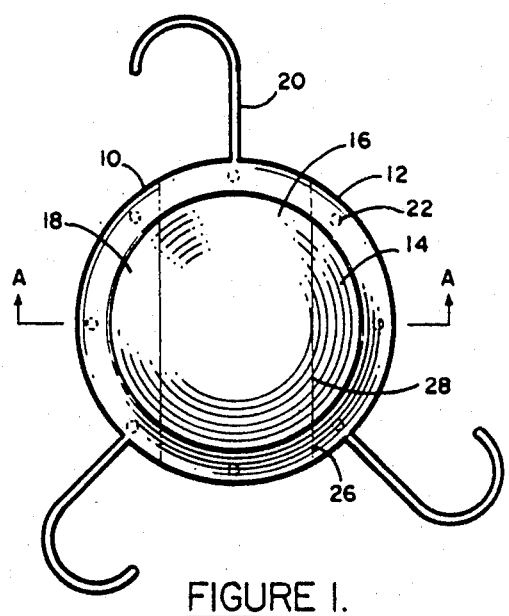
FIG. 1 illustrates a first embodiment of the invention comprising a lens body made up of a plurality of segments secured in a foldable frame member.
Figure 2:
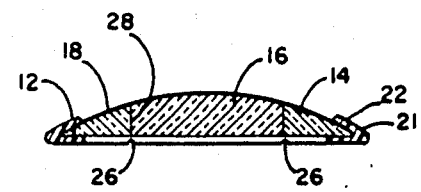
FIG. 2 is a sectional view taken along lines A—A of FIG. 1.
Figure 3:
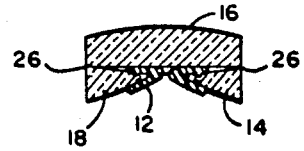
FIG. 3 is a sectional view of the lens of FIGS. 1 and 2 shown in a temporarily distorted condition for being inserted into the eye.
Figure 4:
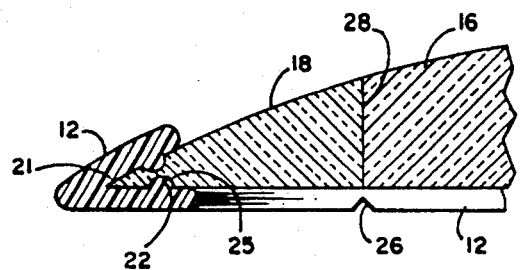
FIG. 4 is an enlarged sectional view of the edge of the lens of FIG. 1 illustrating means for being secured in a frame.

In FIGS. 1–5 there is illustrated a first embodiment in which a flexible, temporarily distortable, and memory retaining frame member holds the assembled lens segments. In FIGS. 1 and 2, the lens 10 comprises a plurality of individual lens segments 14, 16 and 18 held in a frame 12. The frame comprises any biocompatible, flexible, temporarily distortable and memory retaining material such as polypropylene, polymethylmethacrylate, polyamide or silicone material. As also illustrated in FIGS. 2 and 4, the frame 12 is preferably molded or formed with an open recess 21 for receiving the outer edge of the lens segments. It may also be desirable to incorporate additional means for securing the lens segments within the recessed frame, and for this purpose, a plurality of projections 22 may be formed on the interior recess surface of the frame member for being received in depressions formed on the outer surface of the lens segments. Such additional securing means are useful for preventing the lens segments from being pulled out of the frame when it is temporarily distorted. Other retaining means may be suitable for this purpose. For example, the ring and/or the edges of the segments may be heated to create a bond between the ring and segments for retention.

In FIG. 3 there is illustrated a temporarily distorted lens in which the two outside lens body segments 14 and 18 are folded to overlap the center segment 16. Fold lines 26 are formed on the frame member and directly overlie the interfacing edges 28 of abutting segments. As shown in FIG. 1, frame member 12 is provided with four fold lines on each outwardly exposed frame member surface, both anterior and posterior, and these fold lines directly overlie the two interfaces of the three abutting lens segments. Thus, when the lens body is folded and distorted in a configuration as shown in FIG. 3, uniform distortion of the frame member at the fold lines readily enhances the adaptability of the lens for temporarily reducing its size for insertion in a relatively small corneal incision.

Figure 5:
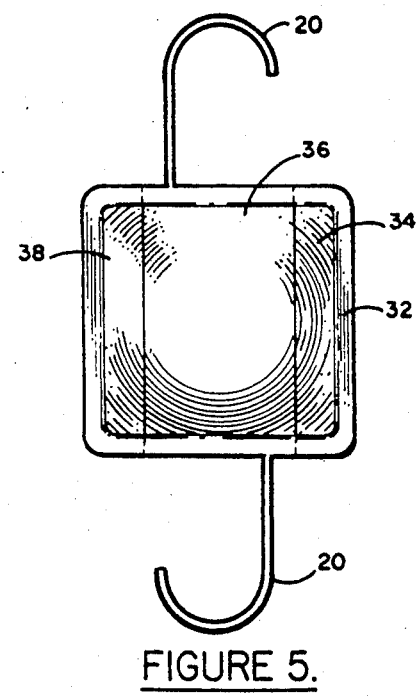
FIG. 5 illustrates a segmented lens body having a different shape secured in a frame member.

A similar lens is illustrated 1n FIG. 5, with the shape of the lens body being rectangular or square. It will be also evident that the three rectangularly shaped lens segments 34, 36 and 38 are retained in a generally rectangular frame member 32, also provided with fold lines which directly overlie the interfacing and abutting surfaces of the respective adjacent lens segments. The frame members of FIGS. 1 and 5 incorporate flexible and memory-retaining support strands 20 for supporting the lens when implanted in the eye, particularly in the posterior chamber. Such support members are further illustrated in my aforesaid prior patent and co-pending application, the descriptions of which are incorporated herein by reference. The number of support strands as well as their shape may also be varied as so disclosed, as may be the shape of the individual lens segments. The frame member in which the segments are secured as well as the shape of the lens body segments may be varied as desired. However, for the purpose of this application, the abutting and interfacing surfaces of the lens segments are preferably parallel to one another and straight as shown in the drawings.

Figures 6, 7:
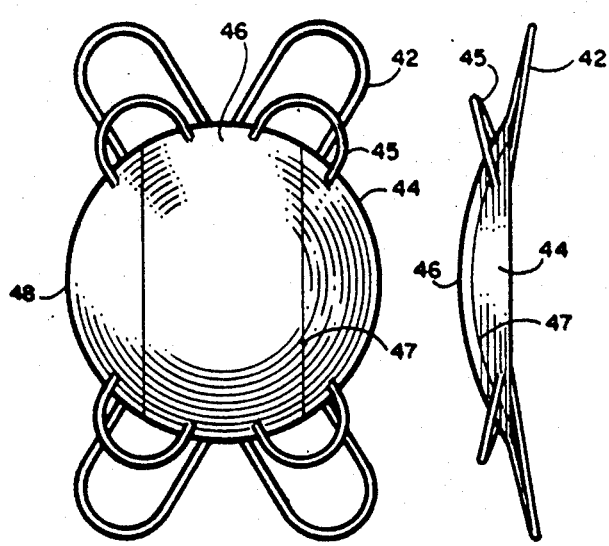
FIG. 6 illustrates another embodiment of the invention comprising a segmented lens held together by a plurality of strand members.
FIG. 7 is a side view of the lens of FIG. 6.

FIGS. 6 and 7 illustrate an embodiment of the invention in which the lens segments are held together in their normal planar relationship with flexible and memory-retaining strands. Any number of strands may be used and their shape is not critical, but it is preferred that each strand is secured in two adjacent lens segments. Thus, in FIG. 6, there are shown differently shaped strands 42 and 45 which secure adjacent lens segments 44 and 46. Moreover, as shown, four of the strands secure two adjacent lens segments thereby providing more substantial retention of the lens segments in the desired planar position. Yet, such segments can be readily folded so that the lens body is temporarily distorted as the two outer segments 44 and 48 are folded in a manner similar to that shown in FIG. 3, and while the lens is being inserted into the eye. Moreover, with the memory-retaining feature of the strands, once the lens is inserted, like the embodiment illustrated in FIGS. 1-5, and pressure to distort the lens body relieved, the lens body will return to take its planar shape in the eye chamber. Suitable strand material will be polypropylene, polymethylmethacrylate, or polyamide. In this embodiment, it is also preferred that a portion of the holding strands be of a size sufficient to act as support members for the lens once it is implanted in the eye. For example, the longer strands 42 will be suitable for supporting the lens in the posterior chamber.

In FIGS. 8 and 9 there is illustrated another embodiment in which the positioning means for holding the lens segments in a normal planar position comprises a plurality of hinges 52. Each hinge preferably includes a fold line 55 which directly overlies interfacing and abutting surfaces 56 of adjacent lens segments. Any suitable means may be used for securing the hinges on the lens segments. For example, projections 54 formed on the hinges and inserted into depressions formed on the surface of the lens body will be useful. The depressions may be formed so that the openings at the lens surface are slightly smaller than the diameter or largest dimension of the hinge projection whereby the projection may be snapped into the depression or cavity for greater stability. Alternatively, the hinge material may be heat bonded to the lens. Any number of the hinges may be used but they are preferably positioned adjacent the outer edge of the lens body to minimize optical interference. The hinges are also preferably of a memory-retaining material which will assist in returning the temporarily folded lens segments to the planar position once the pressure of the distortion is released when the lens body is placed within the eye. A suitable material will be that disclosed for forming the frame member of FIG. 1. The hinges are preferably located on the flat posterior surface 50 of the lens body, as shown.

FIGS. 10 and 11 illustrate another embodiment utilizing a thin flexible membrane 62 of an optical and biocompatible material such as silicone secured to the posterior surface of the lens body 60. Such a material will provide a means for holding the lens segments 61, 63 and 65 together, and allows them to be folded to reduce the size of the corneal incision for insertion of the lens body into the eye. The lens segments may also be easily returned to a planar position inside the eye. The membrane or the thin sheet of optic material may be secured to the surface of the lens segments with a biocompatible glue, or could be heat bonded to the lens.

The segmented lens illustrated in FIGS. 1 and 5 may be also produced by a process in which a laser beam is used to cut the segments while the lens is in the frame. A laser beam would cut through a unitary lens body secured in the frame to create the separate segments, and at the same time be used to inscribe fold lines on the frame member.

The method of inserting the segmented lens described above is well known to those skilled in the art and further described in my aforesaid co-pending application, the description of which is incorporated herein by reference.

Figures 12, 13:
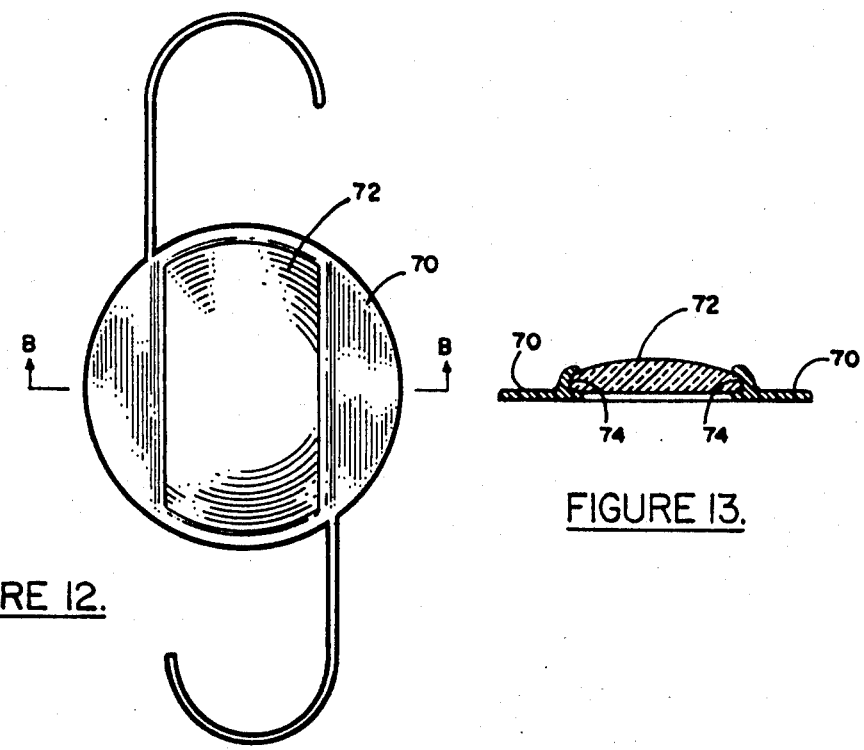
FIGS. 12 and 13 illustrate a single center lens member supported in a modified flexible and foldable frame member, FIG. 13 being a sectional view taken along lines B—B of FIG. 12.

In the embodiment shown in FIGS. 12 and 13 a single lens member 72 is secured in deformable frame 70. The lens segment has a shape like that of a center segment shown in the previous embodiments, again preferably between about 2.5 and 3.5 mm across or in the lateral direction and between about 4 and about 7 mm in the vertical direction. The frame may be ring shaped as shown, having intergral support strands extending therefrom. An interior channel 74 receives the edges of the lens member. The sides of the frame are preferably thin or flattened relative to the thickness of the lens as shown. A suitable frame material is that previously disclosed, while the lens may be a conventional optical lens material such as polymethylmethacrylate or glass, although more highly refractive materials may also be used. Where conventional lens material is used, the thickness will normally be between about 1.5 and 2.5 mm. When the lens is to be inserted, the relatively flat and flexible frame sides are simply temporarily folded to overlap the lens member in a manner as previously described.

I claim:

1. An intraocular lens comprising a segmented lens body comprising a plurality of lens segments normally held in a planar and abutting relationship by flexible, distortable and memory-retaining strand members, each strand member secured in two adjacent lens segments, whereby said lens segments may be temporarily overlapped for insertion through a corneal incision into the eye.

2. An intraocular lens comprising a segmented lens body having a plurality of lens segments having a thickness of about 1.0 mm or less of a material having an index of refraction of about 1.5 or more, each one abutting at least one other lens segment along an interface, said lens segments held together by a plurality of distortable, memory-retaining members, each member being secured in at least two adjacent lens segments, said lens body being temporarily distortable from a first form wherein said lens segments lie in a single plane to a second form wherein said lens segments are overlapped and said members temporarily distorted.

3. The lens of claim 2 wherein said members comprise strands.

* * * * *